US007070124B1

(12) United States Patent
Juo

(10) Patent No.: US 7,070,124 B1
(45) Date of Patent: Jul. 4, 2006

(54) AIRBRUSH

(75) Inventor: Chung-Tsuen Juo, Taichung (TW)

(73) Assignee: Victor Air Tools Co., Ltd., Taichung (TW)

( * ) Notice: Subject to any disclaimer, the term of this patent is extended or adjusted under 35 U.S.C. 154(b) by 0 days.

(21) Appl. No.: 11/124,036

(22) Filed: May 9, 2005

(51) Int. Cl.
*B05B 7/30* (2006.01)
*A62C 13/62* (2006.01)
*A62C 13/66* (2006.01)
*A61M 11/02* (2006.01)

(52) U.S. Cl. ...................... 239/345; 239/340; 239/369; 239/371

(58) Field of Classification Search ................ 239/345, 239/340, 369, 371, 302, 346, 353, 376–378, 239/407, 525
See application file for complete search history.

(56) References Cited

U.S. PATENT DOCUMENTS 1,268,403 A * 6/1918 Stacker ....................... 239/345
1,299,290 A * 4/1919 Berg .......................... 239/346
4,161,289 A * 7/1979 Rebold ....................... 239/346
5,421,518 A * 6/1995 Robisch et al. ............. 239/311
5,961,050 A * 10/1999 Kitajima ..................... 239/346
6,105,881 A * 8/2000 Kitajima ..................... 239/353
6,354,517 B1 * 3/2002 Wu ............................ 239/353

* cited by examiner

*Primary Examiner*—David A. Scherbel
*Assistant Examiner*—Darren Gorman
(74) *Attorney, Agent, or Firm*—Rosenberg, Klein & Lee

(57) ABSTRACT

An airbrush including a nozzle has a first connecting section and a polished second connecting section. A projecting stopper section is disposed between the first and second connecting sections. The second connecting section of the nozzle is inserted in a color outlet of a head section of the nozzle. A ventilating plate is fitted on the first connecting section. The ventilating plate is formed with at least one ventilating section for the air to flow through. A shoulder section is formed in the nozzle cap for pressing the ventilating plate against the stopper section of the nozzle. Accordingly, the second connecting section of the nozzle is fixedly fitted in the color outlet of the head section of the brush body. Therefore, the nozzle is fixedly assembled with the brush body by means of the nozzle cap and the ventilating plate, whereby the nozzle can be quickly and conveniently disassemble/assemble without using any tool.

6 Claims, 6 Drawing Sheets

AIRBRUSH

BACKGROUND OF THE INVENTION

The present invention is related to an airbrush, and more particularly to an airbrush in which the nozzle can be easily installed and detached.

An airbrush is used to color a work piece or a specific region. In accordance to different requirements, the airbrush often needs to eject different colors onto the work piece. In order to avoid mixture of different colors, it is often necessary to wash the nozzle of the airbrush before replacing the color. Also, after a period of use, it is necessary to wash the nozzle of the airbrush to prevent the nozzle from being clogged by the dried color. In the case that the nozzle of the airbrush is uneasy to install or detach, it will be quite inconvenient to use the airbrush.

FIGS. 7 and 8 show a conventional airbrush including a brush body 7 having an internal receiving space 71. The brush body 7 longitudinally has a head section 72 and a tail section 73. The head section 72 has a color outlet 721. The wall of the color outlet 721 is formed with a first threaded section 722.

The airbrush further includes a nozzle 8 formed with a second threaded section 81 corresponding to the first threaded section 722 for screwing the nozzle 8 in the head section 72 of the brush body 7. The nozzle 8 has an ejecting section 82 extending from the second threaded section 81. The ejecting section 82 has a nozzle opening 821. A nozzle cap 83 is screwed around the nozzle 8.

The airbrush further includes a color cup 9 having a containing tank 91 in which a color is contained. The bottom of the containing tank 91 is formed with a color port 93 communicating with the receiving space 71 of the brush body 7.

The airbrush further includes an intake pipe 94 communicating with a passage 941 which further communicates with the nozzle 8. An external high-pressure air can pass through the passage 941 to be ejected from the nozzle 8.

The airbrush further includes a control mechanism 95 disposed in the brush body 7 for controlling the flow way of the nozzle opening 821.

The airbrush further includes an intake mechanism 96 for blocking/unblocking the airflow way of the intake pipe.

The nozzle 8 of the conventional airbrush is screwed in the head section 72 of the brush body 7. In order to avoid leakage of the color, the nozzle 8 is very tightly screwed in the head section 72. Therefore, when it is necessary to wash the nozzle 8, the nozzle 8 cannot be manually unscrewed and a special tool is needed to clamp the ejecting section 82 and unscrew the second threaded section 81 of the nozzle 8 from the first threaded section 722. At this time, the color outlet 721 of the head section 72 and the nozzle opening 821 of the nozzle 8 can be washed. After washed, the above procedure is reversed and the nozzle 8 is screwed into the color outlet 721 of the head section 72 with the special tool.

The above operation is quite troublesome and inconvenient to a user.

SUMMARY OF THE INVENTION

It is therefore a primary object of the present invention to provide an airbrush including a nozzle has a first connecting section and a polished second connecting section. A projecting stopper section is disposed between the first and second connecting sections. The second connecting section of the nozzle is inserted in a color outlet of a head section of the nozzle. A ventilating plate is fitted on the first connecting section. The ventilating plate is formed with at least one ventilating section for high-pressure air to flow through toward the nozzle passage. A shoulder section is formed in the nozzle cap for pressing the ventilating plate against the stopper section of the nozzle. Accordingly, the nozzle is fixedly assembled with the brush body by means of the nozzle cap and the ventilating plate, whereby the nozzle can be quickly and conveniently disassemble/assemble without using any tool.

According to the above object, the airbrush of the present invention includes:

a brush body having an internal receiving space, the brush body longitudinally having a head section and a tail section distal from each other, the head section having a color outlet, a color cup being disposed on the brush body near the head section for containing a color, a bottom of the color cup communicating with the color outlet;

a nozzle disposed in the head section of the brush body, the nozzle having a first connecting section and a second connecting section opposite to the first connecting section, the second connecting section being disposed in the color outlet, the nozzle being formed with a nozzle passage extending through the nozzle from the first connecting section to the second connecting section, the nozzle passage communicating with the color outlet;

a nozzle cap having a first receiving cavity in which the head section is enclosed, the nozzle being received in the first receiving cavity, the nozzle cap being formed with a first opening communicating with the first receiving cavity corresponding to the nozzle, whereby the first connecting section of the nozzle is fitted through the first opening, the nozzle cap being further formed with a third connecting section near the first opening;

an outer cap detachably connected with the third connecting section, the outer cap being formed with a through hole communicating with the nozzle passage;

an airway disposed in the brush body and communicating with the nozzle;

an intake pipe disposed under the brush body and communicating with the airway, whereby an external high-pressure air can pass through the airway and flow to the nozzle;

a control mechanism disposed in the receiving space of the brush body for controlling the flow way of the nozzle passage; and an intake mechanism disposed in the intake pipe for blocking/unblocking the airflow way of the intake pipe.

The nozzle has a projecting stopper section disposed between the first and second connecting sections. A ventilating plate is fitted on the first connecting section. The ventilating plate has a first abutting face and a second abutting face. A through hole passes through the ventilating plate from the first abutting face to the second abutting face. The first connecting section is fitted through the through hole. The ventilating plate is formed with at least one ventilating section. A shoulder section is formed in the first receiving cavity of the nozzle cap for pressing the first abutting face of the ventilating plate, whereby the second abutting face abuts against one side of the stopper section of the nozzle.

The present invention can be best understood through the following description and accompanying drawings wherein:

DETAILED DESCRIPTION OF THE PREFERRED EMBODIMENTS

Figure 1:
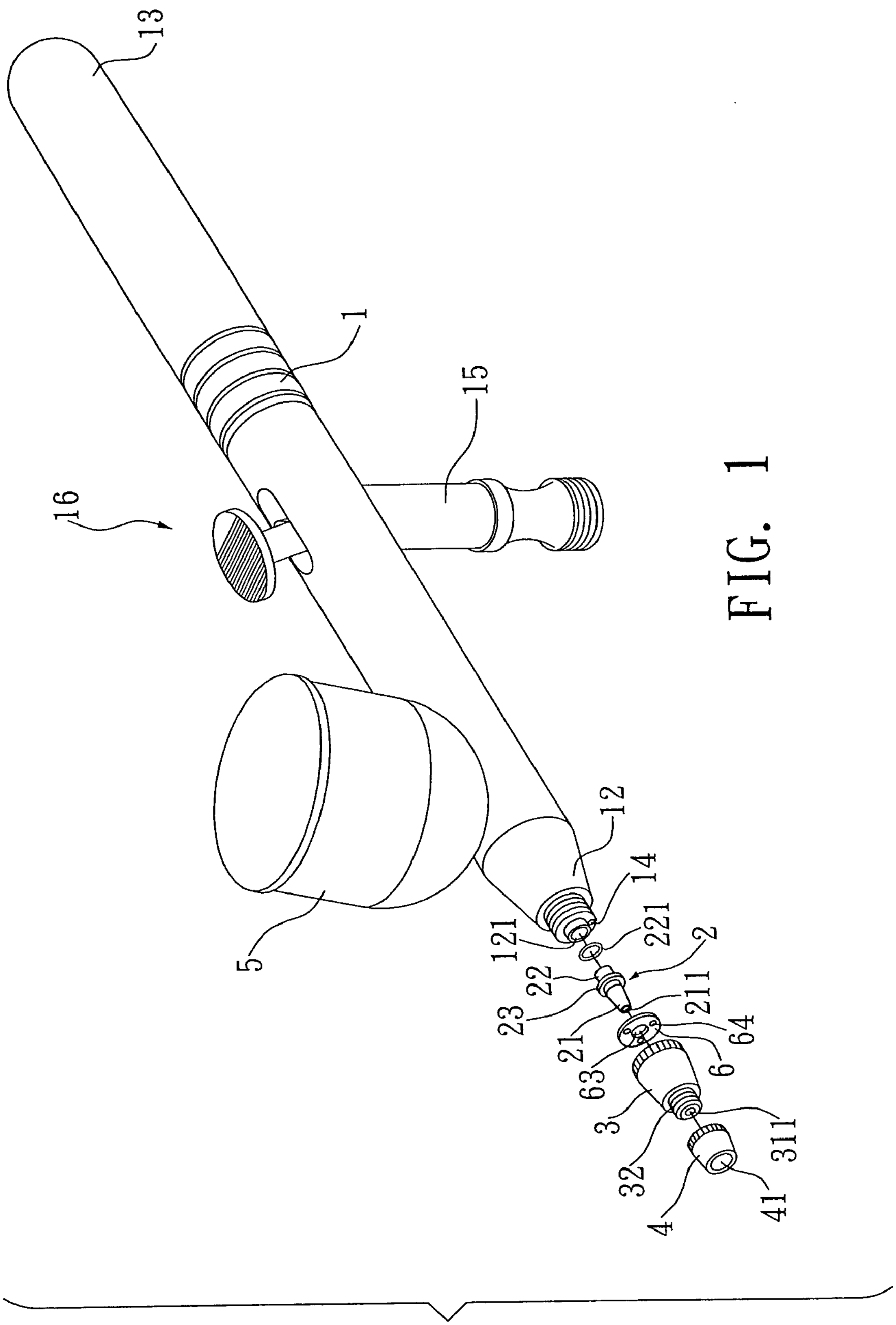
FIG. 1 is a perspective assembled view of the present invention.
Figure 2:
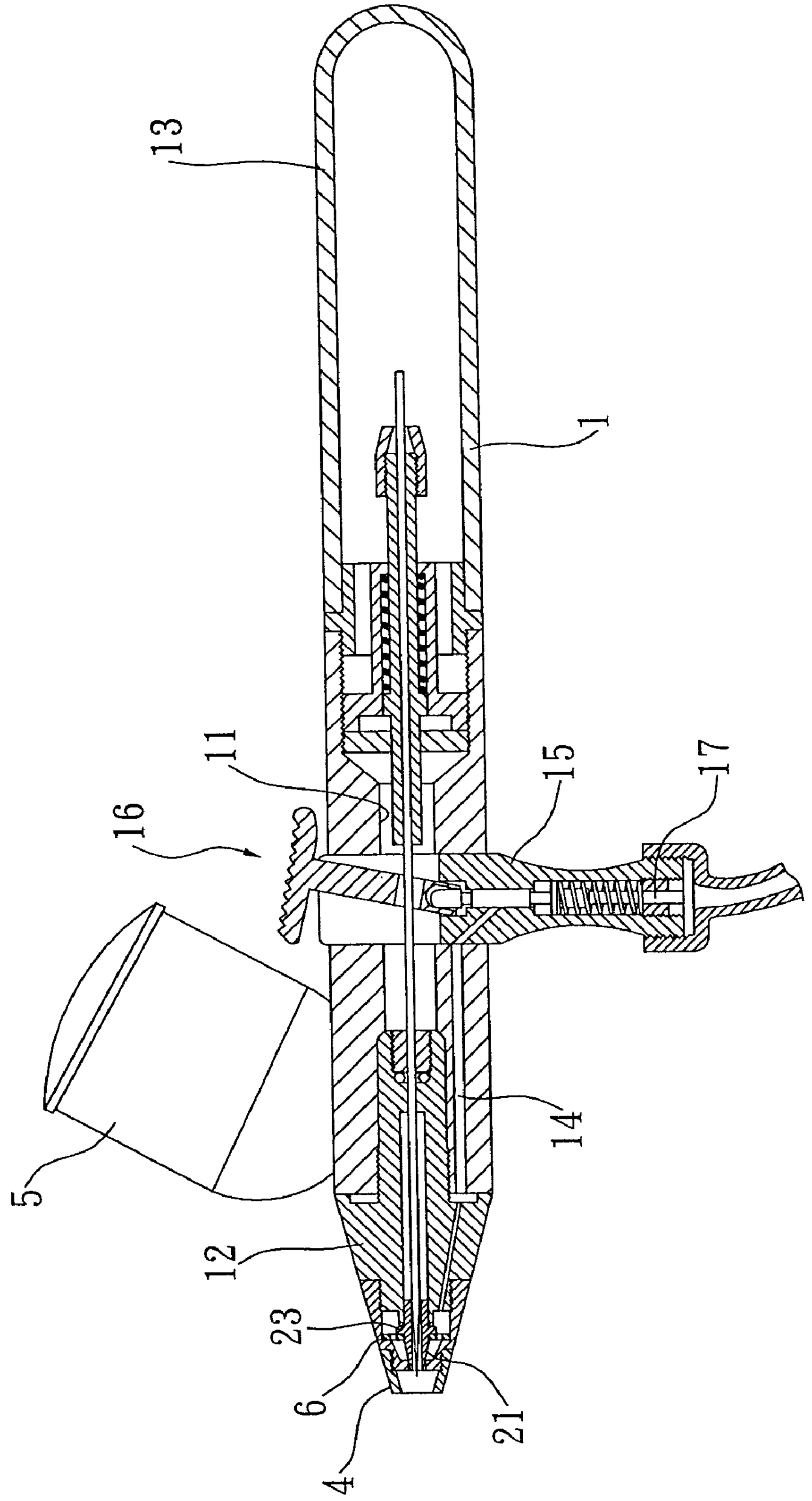
FIG. 2 is a sectional assembled view of the present invention.
Figure 3:
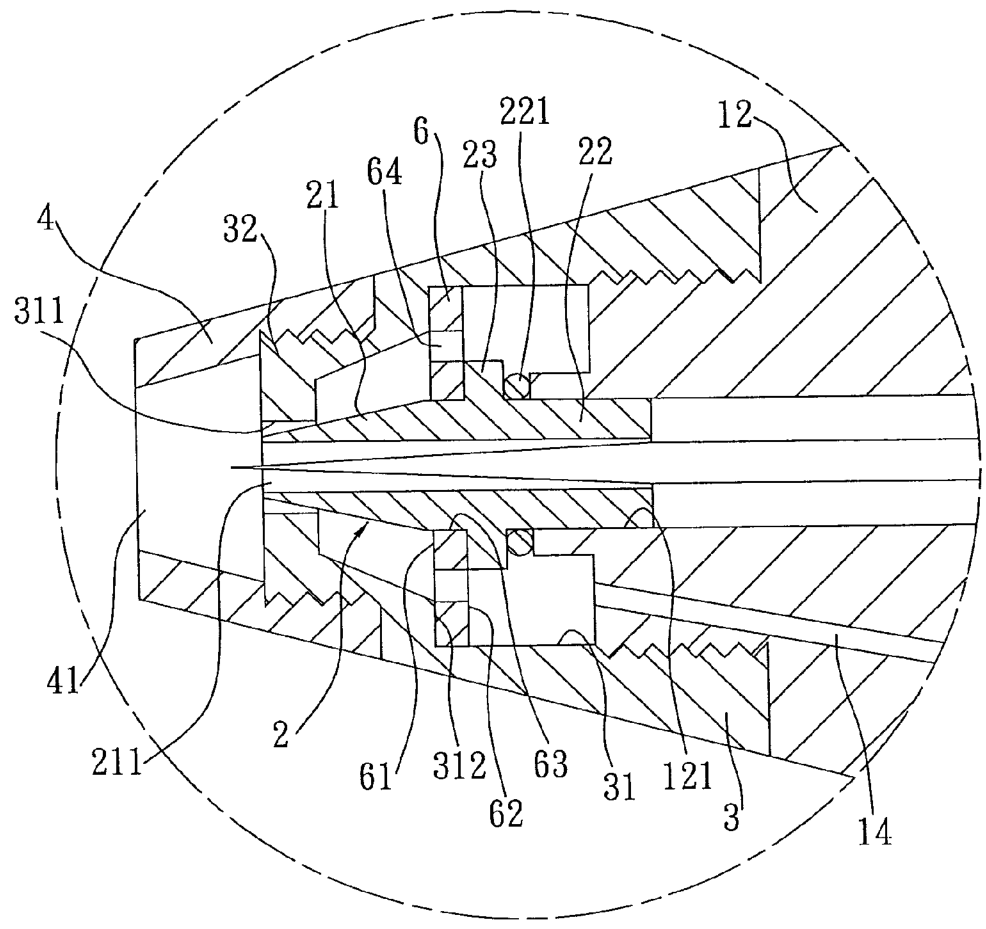
FIG. 3 is an enlarged view of the head section of the brush body of the present invention.
Figure 4:
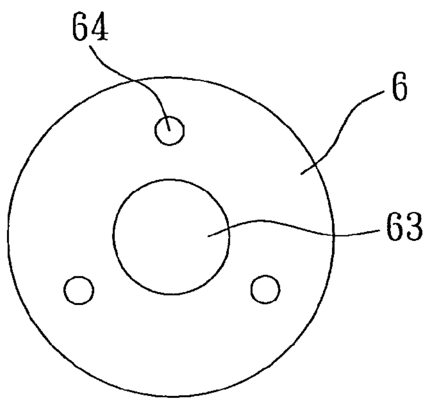
FIG. 4 shows a first embodiment of the ventilating plate of the present invention.

Please refer to FIGS. 1 to 4. According to a preferred embodiment, the airbrush of the present invention includes a brush body 1 having an internal receiving space 11. The brush body 1 longitudinally has a head section 12 and a tail section 13. The head section 12 has a color outlet 121. A color cup 5 is disposed on the brush body 1 near the head section 12 for containing a color. The bottom of the color cup 5 communicates with the color outlet 121.

The airbrush of the present invention further includes a nozzle 2 disposed in the head section 12 of the brush body. The nozzle 2 has a first connecting section 21 and a second connecting section 22 opposite to the first connecting section 21. The second connecting section 22 is disposed in the color outlet 121. The nozzle 2 is formed with a nozzle passage 211 extending through the nozzle 2 from the first connecting section 21 to the second connecting section 22. The nozzle passage 211 communicates with the color outlet 121.

The airbrush of the present invention further includes a nozzle cap 3 having a first receiving cavity 31 in which the head section 12 is enclosed. The nozzle 2 is received in the first receiving cavity 31. The nozzle cap 3 is formed with a first opening 311 communicating with the first receiving cavity 31 corresponding to the nozzle 2. The first connecting section 21 of the nozzle 2 is fitted through the first opening 311. The nozzle cap 3 is further formed with a third connecting section 32 near the first opening 311.

The airbrush of the present invention further includes an outer cap 4 screwed on the third connecting section 32. The outer cap 4 is formed with a through hole 41 communicating with the nozzle passage 211.

The airbrush of the present invention further includes an airway 14 disposed in the brush body 1 and communicating with the nozzle 2.

The airbrush of the present invention further includes an intake pipe 15 disposed under the brush body and communicating with the airway 14. An external high-pressure air can pass through the airway 14 and flow to the nozzle 2.

The airbrush of the present invention further includes a control mechanism 16 disposed in the receiving space 11 of the brush body 1 for controlling the flow way of the nozzle passage 211.

The airbrush of the present invention further includes an intake mechanism 17 disposed in the intake pipe 15 for blocking/unblocking the airflow way of the intake pipe 15.

The nozzle 2 has a projecting stopper section 23 disposed between the first and second connecting sections 21, 22. A ventilating plate 6 is fitted on the first connecting section 21. The ventilating plate 6 has a first abutting face 61 and a second abutting face 62. A through hole 63 passes through the ventilating plate 6 from the first abutting face 61 to the second abutting face 62. The first connecting section 21 is fitted through the through hole 63. The ventilating plate 6 is formed with several ventilating sections. In this embodiment, the ventilating sections are three vents 64 arranged at intervals. The vents 64 pass through the ventilating plate 6 from the first abutting face 61 to the second abutting face 62.

The high-pressure air can flow from the intake pipe 15 through the airway 14 and then flow through the vents 64 to the nozzle passage 211 of the nozzle 2. A shoulder section 312 is formed in the first receiving cavity 31 of the nozzle cap 3 for pressing the first abutting face 61 of the ventilating plate 6, whereby the second abutting face 62 abuts against one side of the stopper section 23 of the nozzle 2. Under such circumstance, the other side of the stopper section 23 tightly abuts against the circumference of the color outlet 121 of the head section 12.

The second connecting section 22 has a polished face fitted in the color outlet 121 of the head section 12. A pad body 221 is fitted around the second connecting section 22 between the stopper section 23 and the circumference of the color outlet 121. In this embodiment, the pad body 221 is an O-ring. By means of the pressing of the ventilating plate 6, the pad body 221 is tightly clamped between the stopper section 23 and the circumference of the color outlet 121 to avoid leakage of the color.

Accordingly, when the intake mechanism 17 is turned on, the external high-pressure air flows into the airway 14 and flows through the vents 64 of the ventilating plate 5 to the nozzle passage 211 of the nozzle 2. At this time, a low pressure is created at the nozzle passage 211. The control mechanism 16 is turned on, whereby the color in the color cup 5 is guided and ejected out of the nozzle passage 211.

The second connecting section 22 of the nozzle 2 is directly fitted in the color outlet 121 of the head section 12 of the brush body and the nozzle 2 is fixed by means of the nozzle cap 3 and the ventilating plate 6. Therefore, when it is necessary to wash the nozzle 2, a user only needs to detach the nozzle cap 3 from head section 12 and sequentially take out the ventilating plate 6 and the nozzle 2 for washing operation.

According to the above arrangement, the user can more quickly and conveniently disassemble/assemble the nozzle 2 without using any tool.

Figure 5:
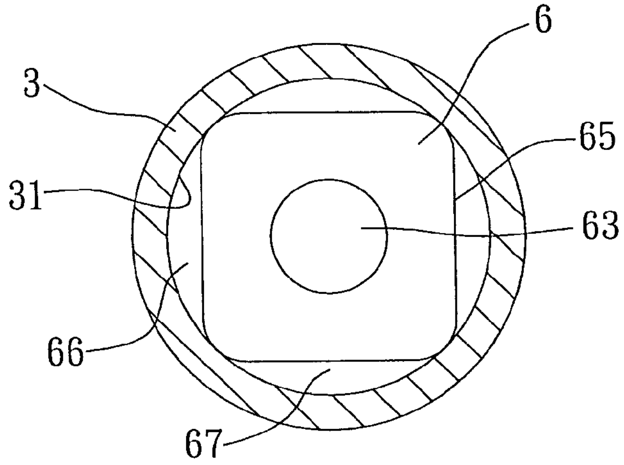
FIG. 5 shows a second embodiment of the ventilating plate of the present invention.

FIG. 5 shows a second embodiment of the present invention, in which the ventilating plate 6 has several straight sides 65. The straight sides 65 and the inner circumference of the first receiving cavity 31 of the nozzle cap 3 define several ventages 67 serving as the ventilating sections for the air to flow through.

Figure 6:
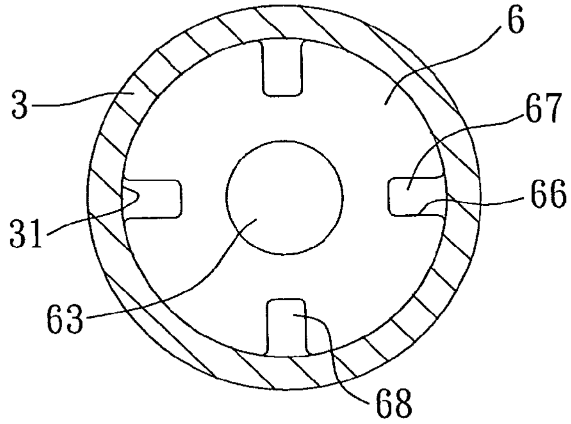
FIG. 6 shows a third embodiment of the ventilating plate of the present invention.
Figure 7:
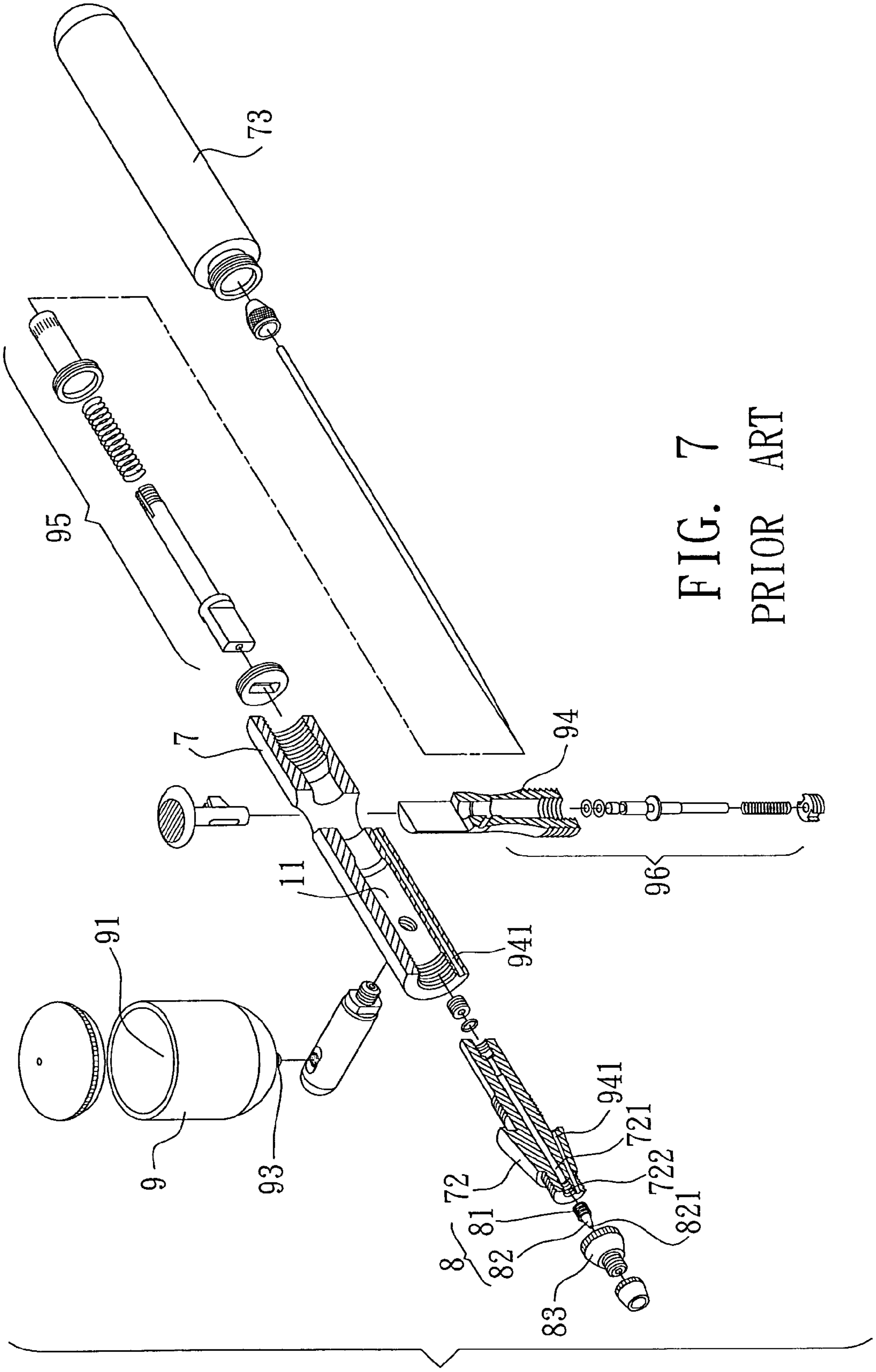
FIG. 7 PRIOR ART
FIG. 7 is a perspective exploded view of a conventional airbrush.
Figure 8:
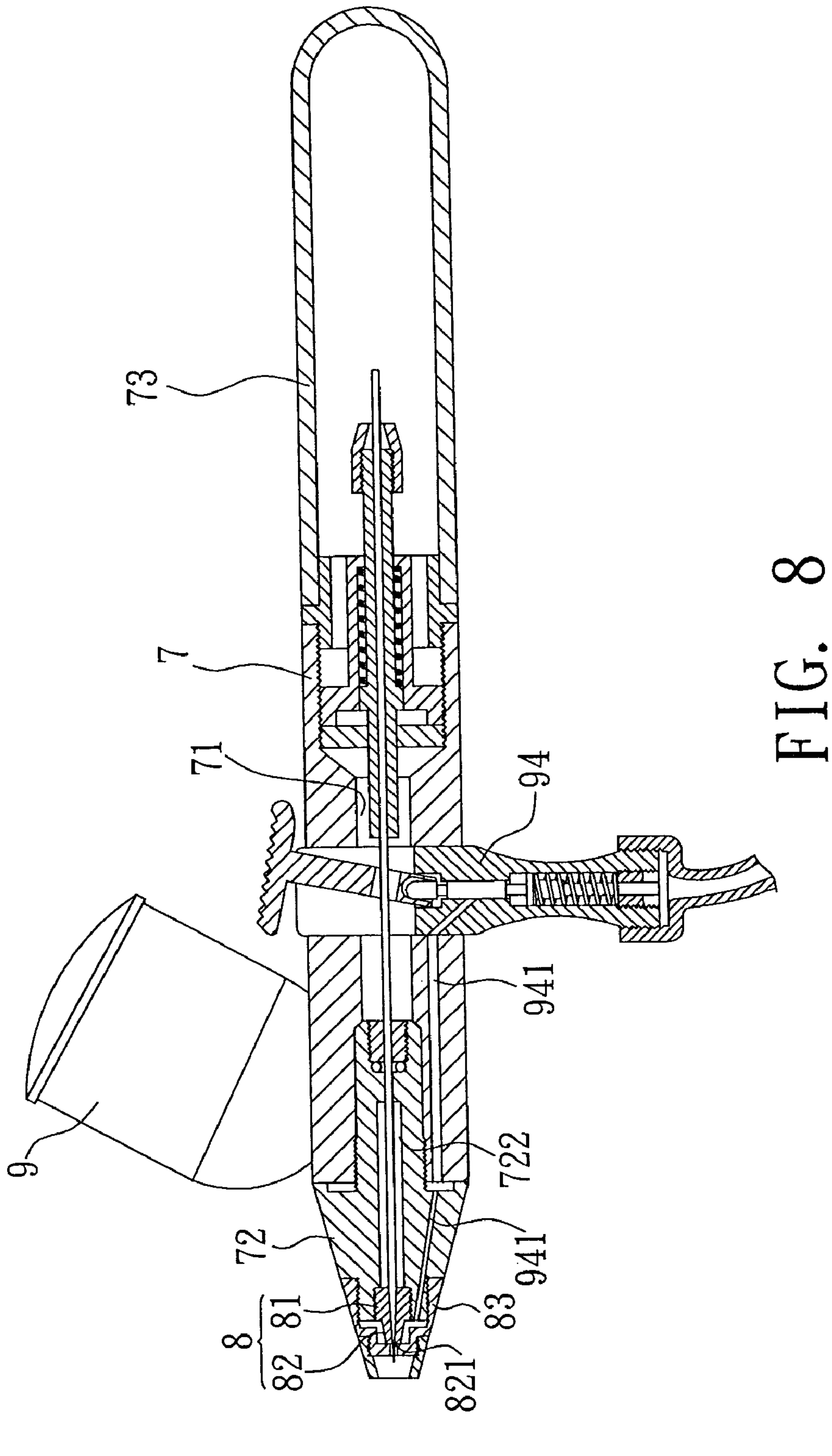
FIG. 8 PRIOR ART
FIG. 8 is a sectional assembled view of the conventional airbrush.

FIG. 6 shows a third embodiment of the present invention, in which the ventilating plate 6 has several notches 66 formed on the circumference at intervals to serve as the ventilating sections 68. The high-pressure air can flow through the ventilating sections 68 to the nozzle passage.

The above embodiments are only used to illustrate the present invention, not intended to limit the scope thereof. Many modifications of the above embodiments can be made without departing from the spirit of the present invention.

What is claimed is:

1. An airbrush comprising:

a brush body having an internal receiving space, the brush body longitudinally having a head section and a tail section distal from each other, the head section having a color outlet, a color cup being disposed on the brush body near the head section for containing a color, a bottom of the color cup communicating with the color outlet;

a nozzle disposed in the head section of the brush body, the nozzle having a first connecting section and a second connecting section opposite to the first connecting section, the second connecting section being disposed in the color outlet, the nozzle being formed with a nozzle passage extending through the nozzle from the first connecting section to the second connecting section, the nozzle passage communicating with the color outlet;

a nozzle cap having a first receiving cavity in which the head section is enclosed, the nozzle being received in the first receiving cavity, the nozzle cap being formed with a first opening communicating with the first receiving cavity corresponding to the nozzle, whereby the first connecting section of the nozzle is fitted through the first opening;

an airway disposed in the brush body and communicating with the nozzle;

an intake pipe disposed under the brush body and communicating with the airway, whereby an external high-pressure air can pass through the airway and flow to the nozzle;

a control mechanism disposed in the receiving space of the brush body for controlling the flow way of the nozzle passage; and an intake mechanism disposed in the intake pipe for blocking/unblocking the airflow way of the intake pipe, said airbrush being characterized in that the nozzle has a projecting stopper section disposed between the first and second connecting sections, a ventilating plate being fitted on the first connecting section, the ventilating plate having a first abutting face and a second abutting face, a through hole passing through the ventilating plate from the first abutting face to the second abutting face, the first connecting section being fitted through the through hole, the ventilating plate being formed with at least one ventilating section, a shoulder section being formed in the first receiving cavity of the nozzle cap for pressing the first abutting face of the ventilating plate, whereby the second abutting face abuts against one side of the stopper section of the nozzle to make the other side of the stopper section tightly abut against a circumference of the color outlet of the head section.

2. The airbrush as claimed in claim 1, wherein the ventilating sections of the ventilating plate are several vents passing through the ventilating plate.

3. The airbrush as claimed in claim 1, wherein the ventilating plate has several straight sides, the straight sides and the inner circumference of the first receiving cavity of the nozzle cap defining several ventages serving as the ventilating sections for the air to flow through.

4. The airbrush as claimed in claim 1, wherein the ventilating plate has several notches formed on the circumference of the ventilating plate at intervals to serve as the ventilating sections for the air to flow through.

5. The airbrush as claimed in claim 1, wherein a pad body is fitted around the second connecting section between the stopper section and the circumference of the color outlet, whereby by means of the pressing of the ventilating plate, the pad body is tightly clamped between the stopper section and the circumference of the color outlet.

6. The airbrush as claimed in claim 5, wherein the pad body is an O-ring.

* * * * *